(12) United States Patent
Peterson et al.

(10) Patent No.: US 9,763,674 B2
(45) Date of Patent: Sep. 19, 2017

(54) ULTRASONIC BONE CUTTING INSTRUMENT

(71) Applicants: Joseph Peterson, Malvern, PA (US); Matthew L. Parsons, Dartmouth, MA (US); Cory G. Kimball, Hamilton, OH (US); Foster B. Stulen, Mason, OH (US); Ashvani K. Madan, Mason, OH (US); Roman Lomeli, Raynham, MA (US)

(72) Inventors: Joseph Peterson, Malvern, PA (US); Matthew L. Parsons, Dartmouth, MA (US); Cory G. Kimball, Hamilton, OH (US); Foster B. Stulen, Mason, OH (US); Ashvani K. Madan, Mason, OH (US); Roman Lomeli, Raynham, MA (US)

(73) Assignee: Ethicon LLC, Guaynabo, PR (US)

( * ) Notice: Subject to any disclaimer, the term of this patent is extended or adjusted under 35 U.S.C. 154(b) by 628 days.

(21) Appl. No.: 14/140,681

(22) Filed: Dec. 26, 2013

(65) Prior Publication Data
US 2015/0182232 A1 Jul. 2, 2015

(51) Int. Cl.
*A61B 17/00* (2006.01)
*A61B 17/16* (2006.01)
*A61B 17/32* (2006.01)

(52) U.S. Cl.
CPC ...... *A61B 17/1624* (2013.01); *A61B 17/1604* (2013.01); *A61B 17/320068* (2013.01); *A61B 2017/320076* (2013.01); *A61B 2017/320084* (2013.01); *A61B 2217/007* (2013.01)

(58) Field of Classification Search
None
See application file for complete search history.

(56) References Cited

U.S. PATENT DOCUMENTS

| | | |
|---|---|---|
| 5,188,102 A | 2/1993 | Idemoto et al. |
| 5,322,055 A | 6/1994 | Davison et al. |
| 5,324,299 A | 6/1994 | Davison et al. |
| 5,873,873 A | 2/1999 | Smith et al. |
| 5,980,510 A | 11/1999 | Tsonton et al. |
| 6,325,811 B1 | 12/2001 | Messerly |
| 6,423,082 B1 | 7/2002 | Houser et al. |

(Continued)

FOREIGN PATENT DOCUMENTS

WO  WO 2007/019870  2/2007

OTHER PUBLICATIONS

International Search Report and Written Opinion dated Aug. 24, 2015 for Application No. PCT/US2014/072050.

(Continued)

*Primary Examiner* — Sameh Boles
(74) *Attorney, Agent, or Firm* — Frost Brown Todd LLC

(57) ABSTRACT

A system includes an ultrasonic instrument and a bone insertion element. The instrument includes an ultrasonic transducer and an ultrasonic blade. The ultrasonic transducer is operable to convert electrical power into ultrasonic vibrations. The ultrasonic blade is in acoustic communication with the ultrasonic transducer such that the ultrasonic transducer drives the ultrasonic blade to vibrate ultrasonically to form an opening within bone. The bone insertion element is configured to be inserted within the opening formed by the ultrasonic blade.

19 Claims, 15 Drawing Sheets

(56) References Cited

U.S. PATENT DOCUMENTS

| | | |
|---|---|---|
| 6,443,969 B1 | 9/2002 | Novak et al. |
| 6,773,444 B2 | 8/2004 | Messerly |
| 6,783,524 B2 | 8/2004 | Anderson et al. |
| 8,043,308 B2 | 10/2011 | Bittenson |
| 8,118,823 B2 | 2/2012 | Cotter et al. |
| 8,277,464 B2 | 10/2012 | Bittenson |
| 8,461,744 B2 | 6/2013 | Wiener et al. |
| 8,591,536 B2 | 11/2013 | Robertson |
| 8,623,027 B2 | 1/2014 | Price et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0065083 A1* | 3/2008 | Truckai ............. A61B 17/3472 600/407 |
| 2008/0194999 A1 | 8/2008 | Yamada et al. |
| 2008/0200940 A1 | 8/2008 | Eichmann et al. |
| 2010/0069940 A1 | 3/2010 | Miller et al. |
| 2010/0076503 A1* | 3/2010 | Beyar ................ A61B 17/1615 606/86 R |
| 2010/0167235 A1 | 7/2010 | Vercellotti |
| 2011/0087212 A1 | 4/2011 | Aldridge et al. |
| 2012/0095472 A1 | 4/2012 | Young |
| 2012/0112687 A1 | 5/2012 | Houser et al. |
| 2012/0116265 A1 | 5/2012 | Houser et al. |
| 2013/0184711 A1 | 7/2013 | Rad |
| 2014/0005701 A1 | 1/2014 | Olson et al. |

OTHER PUBLICATIONS

U.S. Appl. No. 13/657,553, filed Oct. 22, 2012.
U.S. Appl. No. 61/410,603, filed Nov. 5, 2010.

\* cited by examiner

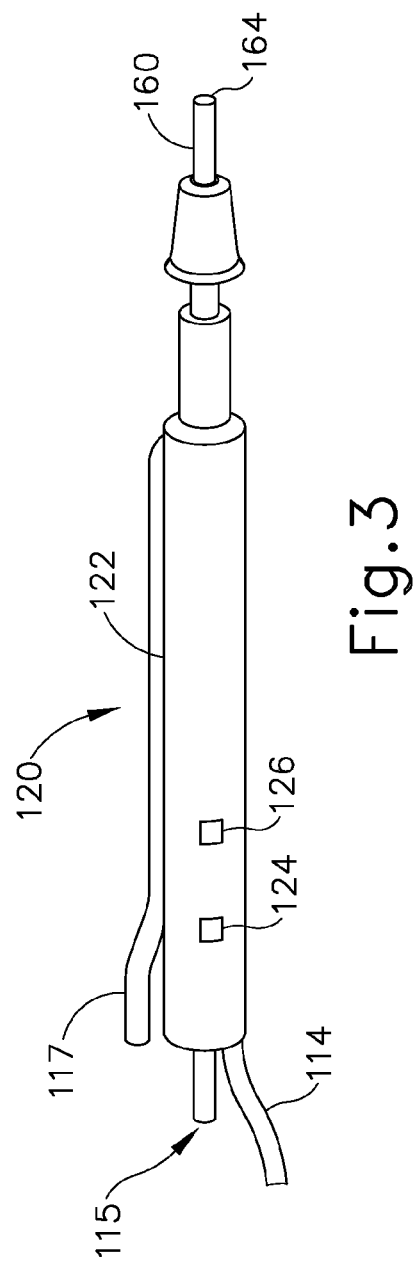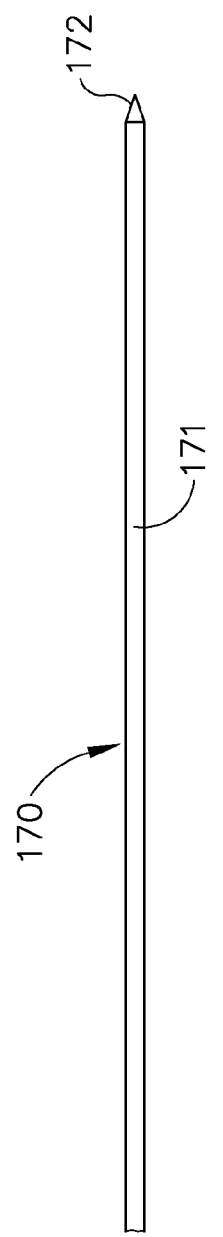

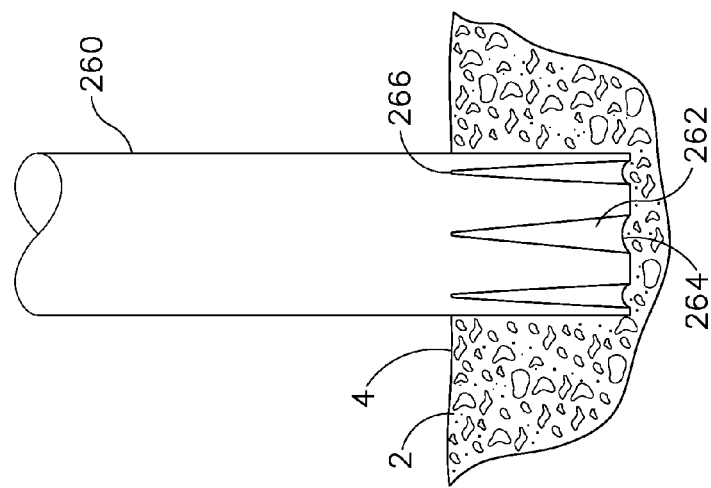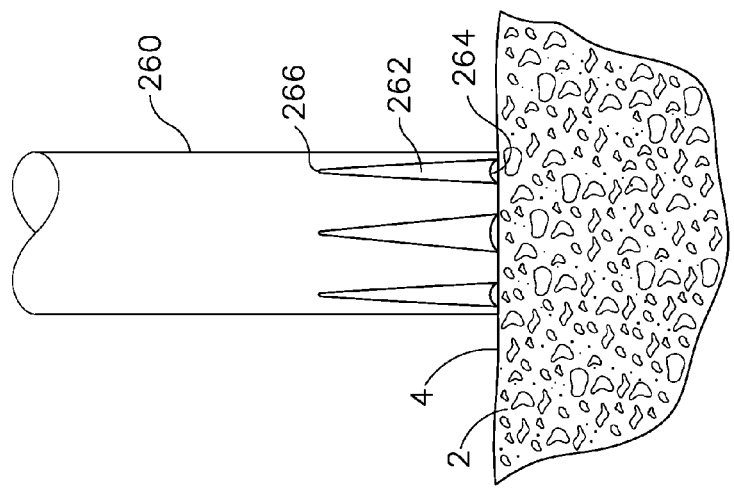
Fig.10B
Fig.10A

ULTRASONIC BONE CUTTING INSTRUMENT

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, now U.S. Pat. No. 8,623,027, issued on Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued on Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued on Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," now U.S. Pat. No. 9,095,367, issued on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts a side perspective view of the instrument of FIG. 2, with a K-wire omitted;

FIG. 4 depicts a side elevational view of a K-wire that may be used with the instrument of FIG. 2;

FIG. 10A depicts a side elevational view of the blade of FIG. 8 engaging a pedicle of a vertebra, with the pedicle shown in cross-section;

FIG. 10B depicts a side elevational view of the blade of FIG. 8 inserted within the pedicle, with the pedicle shown in cross-section;

Figure 1:
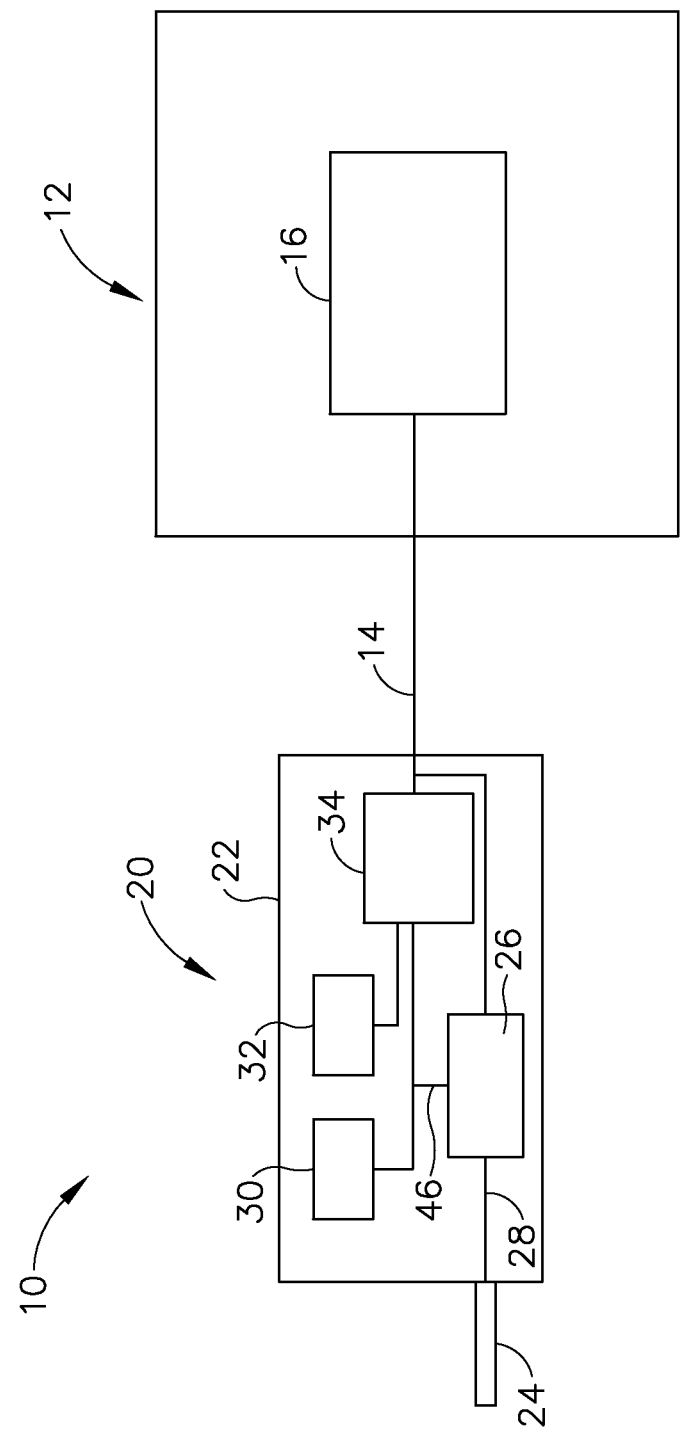
FIG. 1 depicts a block schematic view of an exemplary ultrasonic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04 or GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes HF105 and DH105 by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Exemplary Ultrasonic Bone Cutting Instrument

The following discussion relates to various exemplary components and configurations for instrument (20) and components thereof. It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

In some instances, it may be desirable to use a version of instrument (20) to cut through bone or otherwise cut into bone. By way of example only, a version of instrument (20) may be used to cut through or into a portion of a vertebra in a patient's spinal column. Alternatively, a version of instrument (20) may be used to cut through or into some other bony structure in a patient. Cutting through or into bone may be desirable in various kinds of procedures. By way of example only, a version of instrument (20) may be used to cut through or into bone to form a channel for inserting a Kirschner wire (also known as a "K-wire"), such as to provide fixation of fractured bone, to provide a guide element for insertion of another component or series of components (e.g., a Jamshidi needle, cannulated pedicle screw, etc.) into the bone, and/or for various other purposes.

A K-wire may be threaded into the bone or impacted into the bone. In some instances, a K-wire is not used, such that a version of instrument (20) may be used to cut through or into bone to form a channel for directly inserting a screw, some other kind of fastener, or a feature of an implant device; to remodel the bone for any suitable purpose; and/or for various other reasons.

In instances where a K-wire is used as a guide for another component, the K-wire may be removed from the bone after the other component (or components) is (or are) suitably positioned in the bone. Various components may be guided along an inserted K-wire in a sequence during a surgical procedure. An example of such a procedure is a pedicle cannulation procedure. In an exemplary pedicle cannulation procedure, after a K-wire has been inserted in a pedicle of a patient's vertebra, a cannulated tapping instrument may be passed along the K-wire to tap an opening in the bone. The tapping instrument may then be removed from the K-wire; and a cannulated screw may then be advanced along the K-wire to thread the screw into the tapped opening. The K-wire may be removed from the bone before or after the cannulated screw is suitably threaded into the tapped opening. After the cannulated screw is secured in the pedicle, along with other cannulated screws in other pedicles, a rod may be secured to two or more of the cannulated screws to provide posterior stabilization of spinal vertebrae. In some instances, a plurality of cannulated screws and rods are used in a single spinal column.

The examples described below relate to various versions of instrument (20) that may be used to cut through or into bone. While the bone-cutting example described above is in the context of a pedicle cannulation procedure, it should be understood that versions of instrument (20) may be used to cut bone in various other clinical contexts. For instance, versions of instrument (20) may be used to drive bone staples or other kinds of bone fixation implants. Of course, the versions of instrument (20) described herein may alternatively be used for other purposes, in addition to or in lieu of cutting bone. It should also be understood that the versions of instrument (20) described below may be used under fluoroscopic guidance and/or using any other suitable form of visualization. Fluoroscopy and/or some other imaging technology may facilitate percutaneous use of an ultrasonic instrument such as instrument (20) to cut into bone in a minimally invasive surgical procedure. The variations of instrument (20) described below may thus be configured for compatibility with fluoroscopy and/or other imaging technology.

A. Exemplary K-Wire Introduction Assemblies

Figure 2:
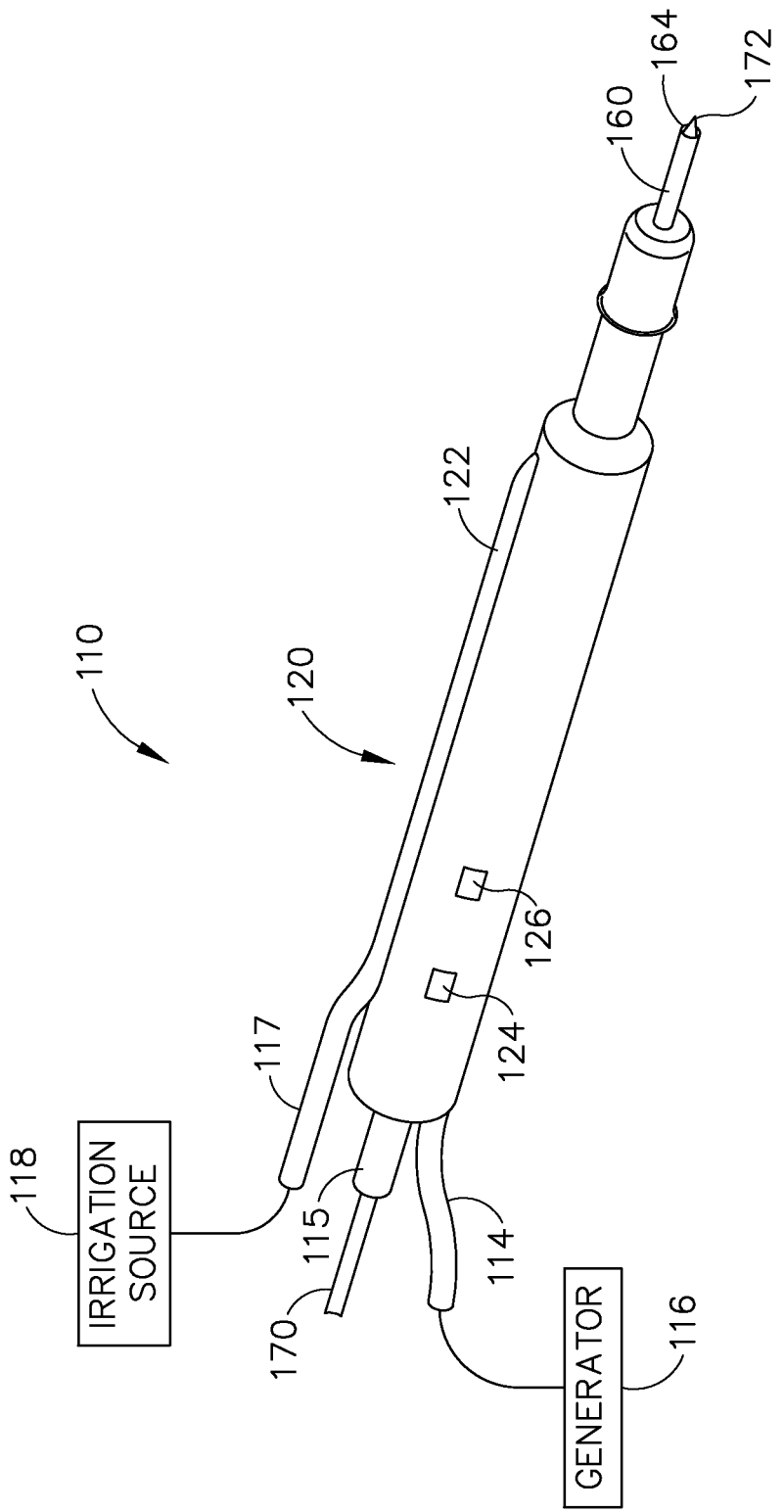
FIG. 2 depicts a perspective view of an exemplary ultrasonic surgical instrument that may form part of the system of FIG. 1.

FIG. 2 shows an exemplary K-wire introduction assembly (110) that comprises an ultrasonic instrument (120), a generator (116), an irrigation fluid source (118), and a K-wire (170). Instrument (120) is configured to operate similar to a Jamshidi needle, but relying more on ultrasonic vibrations and less on axially oriented pushing force to promote insertion into bone. In other words, ultrasonic capabilities of instrument (120) may eliminate the need for a mallet, which might otherwise be needed in order to drive a conventional Jamshidi needle into bone. The ultrasonic facilitation of bone penetration by instrument (120) may provide more precise placement of a K-wire (170), may reduce the operating room time required to place K-wire (170), and may reduce the exposure of the patient and operating room staff to radiation from imaging equipment that may be used to provide visualization during use of instrument (120).

Instrument (120) is coupled with generator (116) via cable (114); and with irrigation source (118) via conduit (117).

Instrument (120) and generator (116) are similar to instrument (20) and generator (12) of surgical system (10) in that instrument (120) is operable to provide ultrasonic vibration in response to power from generator (116). As best seen in FIG. 3, instrument (120) comprises a handpiece (122) that is similar to handpiece (22). While handpiece (122) has an elongate, cylindraceous configuration in this example, it should be understood that handpiece (122) may have any other suitable configuration.

A hollow, tubular blade (160) extends distally from handpiece (122). As described below, tubular blade (160) is configured to operate similar to a trephine of a Jamshidi needle. Handpiece (122) houses an ultrasonic transducer (not shown) and a waveguide (not shown) that are similar to transducer (26) and waveguide (28) described above. The waveguide provides an acoustic coupling between the transducer and blade (160). The transducer of instrument (120) is operable to convert electrical power from generator (116) into ultrasonic vibrations. These ultrasonic vibrations are communicated to blade (160) via the waveguide, such that ultrasonic energy is delivered to blade (160) through the transducer and waveguide when powered by generator (116). In the present example, generator (116) is activated to provide power to instrument (120) by pressing button (124) on handpiece (122). While handpiece (122) has just one button (124) in this example, it should be understood that any other suitable number of buttons may be provided. For instance, different buttons may be associated with different power levels. It should also be understood that various other kinds of features may be provided to activate generator (116) as will be apparent to one with ordinary skill in the art in view of the teachings herein.

Blade (160) of the present example has a hollow, tubular shape such that blade (160) defines a lumen (162) (e.g., similar to the trephine of a Jamshidi needle). The distal edge (164) of blade (160) is circular in this example, such that distal edge (164) extends along a plane that is perpendicular to the longitudinal axis of blade (160), though it should be understood that any other suitable configuration may be provided. It should also be understood that distal edge (164) may be blunt, sharp, serrated, or otherwise configured. In the present example, distal edge (164) is located at a position corresponding to an anti-node associated with resonant ultrasonic vibrations communicated through blade (160) and the waveguide of instrument (120). Thus, when blade (160) is activated with ultrasonic energy, distal edge (164) vibrates ultrasonically. By way of example only, this vibration may include longitudinal displacement, transverse displacement, and/or torsional displacement in relation to the longitudinal axis of blade (160).

Irrigation fluid source (118) may be used to provide fluid irrigation at the surgical site. Such irrigation may assist with providing a cooling effect, flushing away debris, and/or providing other results. By way of example only irrigation fluid source may provide saline as an irrigation fluid. Such fluid may be driven by gravity, by a pump, by ultrasonic vibrations of blade (160) and/or in any other suitable fashion. Irrigation source (118) provides fluid to blade (160) through conduit (117) extending through handpiece (122). At least a portion of conduit (117) may extend through lumen (162) of blade (160) and/or adjacent to the exterior of blade (160). As yet another merely illustrative example, conduit (117) may distally terminate at lumen (162), such that fluid from irrigation fluid source (118) is communicated into lumen (162) via conduit (117). Other suitable arrangements will be apparent to those of ordinary skill in the art in view of the teachings herein. Irrigation source (118) is selectively activated by pressing button (126) on handpiece (122) in the present example. Of course, any other suitable kind of user input feature may be used to selectively activate irrigation source (118).

Instrument (120) of the present example further comprises a K-wire port (115) at the proximal end of handpiece (122). K-wire port (115) is sized and configured to insertingly receive a conventional K-wire (170). K-wire port (115) is coaxially aligned with lumen (162) of blade (160); and is also in communication with lumen (162). K-wire port (115) thus provides a channel for inserting K-wire (170) through lumen (162). In some other versions, K-wire port (115) is longitudinally offset from and/or angled obliquely or transversely relative to the longitudinal axis of lumen (162) of blade (160). In some such versions, the sidewall of blade (160) includes an opening that is in communication with K-wire port (115), enabling a K-wire (170) that is inserted through K-wire port (115) to enter lumen (162) of blade (160) despite the offset, oblique, and/or transverse relationship between K-wire port (115) and the longitudinal axis of lumen (162) of blade (160). It should be understood that blade (160) acts as a guide shaft for K-wire (170), such that blade (160) is used to guide K-wire (170) into a pedicle (2) as described in greater detail below.

As shown in FIG. 4, K-wire (170) comprises a shaft (171) having a sharp tip (172) at the distal end of shaft (171). In some versions, the inner diameter of blade (160) is less than the outer diameter of K-wire (170), such that fluid from irrigation fluid source (118) may flow through a gap defined between the inner diameter of blade (160) is less than the outer diameter of K-wire (170) when K-wire (170) is disposed in lumen (162).

Figure 5C:
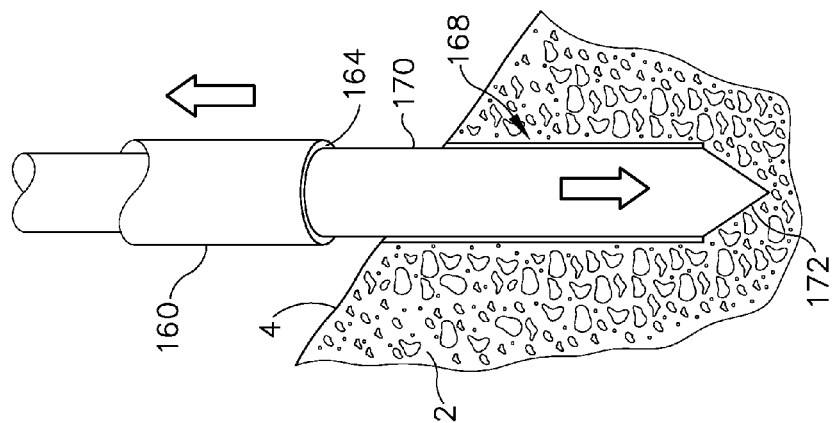
FIG. 5C depicts a side elevational view of the blade of FIG. 5A being removed from the pedicle, leaving the K-wire of FIG. 4 inserted in the pedicle, with the pedicle shown in cross-section.
Figure 5B:
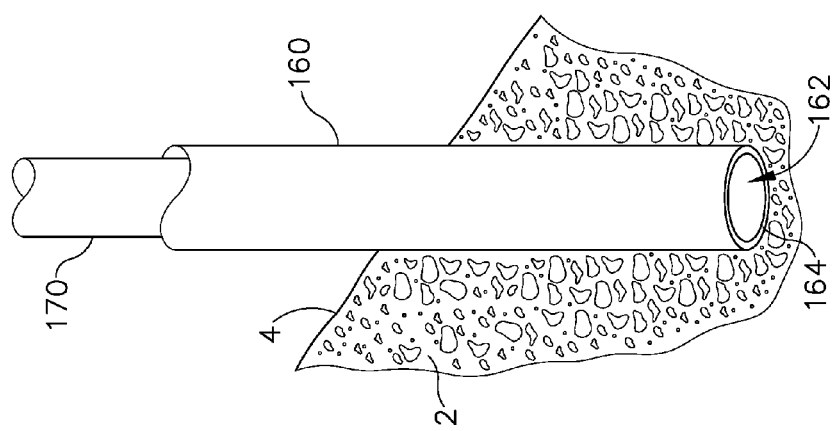
FIG. 5B depicts a side elevational view of the blade of FIG. 5A further inserted within the pedicle, with the pedicle shown in cross-section.
Figure 5A:
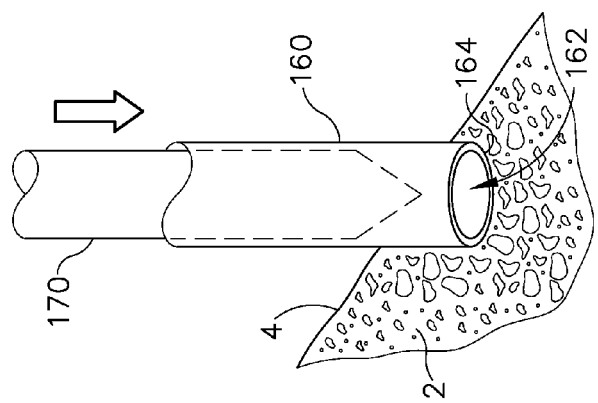
FIG. 5A depicts a side elevational view of a blade of the instrument of FIG. 2 being inserted within a pedicle of a vertebra, with the pedicle shown in cross-section.

As noted above, blade (160) may be used to cut into bone. For instance, FIGS. 5A-5C show instrument (120) being used to insert K-wire (170) into a pedicle (2) of a patient's vertebra. Of course, instrument (120) may instead be used to cut bone and/or other anatomical features elsewhere within a patient. In the present example, instrument (120) is advanced toward pedicle (2) with K-wire (170) retracted within blade (160), as shown in FIG. 5A. Tip (172) of K-wire (170) is proximal to distal edge (164), such that tip (172) does not protrude distally from blade (160). In some instances, such as when instrument (120) is used in a minimally invasive surgical procedure, blade (160) penetrates through the patient's skin, fascia, and muscle before reaching the outer surface (4) of pedicle (2) as shown in FIG. 5A. The longitudinal axis of blade (160) may be aligned with the axis of pedicle (2) (e.g., similar to the orientation shown in FIG. 7). Blade (160) is activated with ultrasonic vibrations, by actuating button (124), as distal edge (164) is driven distally into pedicle (2). These ultrasonic vibrations promote penetration of the bone of pedicle (2) by blade (160). It should be understood that blade (160) may penetrate the bone of pedicle (2) even when distal edge (164) is oriented obliquely relative to the outer surface (4) of pedicle (2) as shown in FIG. 5A. The configuration of blade (160) and/or the ultrasonic vibration of blade (160) may prevent distal edge (164) from skiving or slipping along the outer surface (4) of pedicle (2).

While still being activated ultrasonically, blade (160) is advanced further distally into pedicle (2) as shown in FIG. 5B. Distal edge (164) is driven substantially beneath the outer surface (4) of pedicle (2). As blade (160) is advanced to the position shown in FIG. 5B, fluid from irrigation fluid source (118) may be communicated through lumen (162) to distal edge (164), such as by actuating button (126). It should also be understood that K-wire (170) may be disposed within lumen (162) as blade (160) is advanced to the position shown in FIG. 5B. For instance, K-wire (170) may advance distally relative to pedicle (2) with blade (160), in a concomitant fashion. Alternatively, K-wire (170) may stay stationary relative to pedicle (2) as blade (160) is advanced to the position shown in FIG. 5B.

In versions where K-wire (170) is disposed in lumen (162) while blade (160) is ultrasonically activated, it should be understood that blade (160) and/or one or more other portions of instrument (120) may include one or more features that provide spacing between K-wire (170) and blade (160), such that ultrasonic vibrations from blade (160) are not transmitted to K-wire (170). For instance, a plurality of nodal supports may be located within lumen (162), at locations corresponding to nodes of ultrasonic vibrations that are communicated through blade (160). Such nodal supports may engage K-wire (170) to prevent K-wire (170) from contacting non-nodal regions of blade (160). In still other versions, instrument (120) may be configured and operated such that K-wire (170) is simply not disposed in lumen (162) when blade (160) is activated ultrasonically. For instance, blade (160) may have no additional component inserted in lumen (162) during the stages shown in FIGS. 5A-5B. As another merely illustrative example, blade (160) may have an obturator or other component inserted in lumen (162) during the stages shown in FIGS. 5A-5B. After reaching the stage shown in FIG. 5B, such a component may be withdrawn from lumen (162) to allow subsequent insertion of K-wire (170) in lumen (162).

Once blade (160) has been driven to a suitable depth within pedicle (2), blade (160) may then be retracted proximally from pedicle (2), leaving K-wire (170) in pedicle (2) as shown in FIG. 5C. In some instances, K-wire (170) is advanced distally, before, while, and/or after blade (160) is retracted proximally. K-wire (170) is thus left in the bore (168) that was formed in pedicle (2) by blade (160). While K-wire (170) is shown as being inserted into bore (168) via lumen (162) in this example, it should be understood that K-wire (170) may be inserted into bore (168) in some other fashion. For instance, K-wire (170) may be inserted into bore (168) after blade (160) has been completely removed from bore (168). It should also be understood that K-wire (170) may be threaded deeper into pedicle (2), further than the distal end of bore (168), if desired. Other suitable methods for inserting K-wire (170) into pedicle (2) will be apparent to one with ordinary skill in the art in view of the teachings herein.

It should also be understood that the process shown in FIGS. 5A-5C may be performed under visual guidance provided by fluoroscopic imaging and/or using other visualization/imaging techniques. Furthermore, the process shown in FIGS. 5A-5C may be performed in both pedicles (2) of a given vertebra. The process may be repeated in as many vertebrae as desired. Once K-wires (170) have been suitably disposed in pedicles (2), various other components (e.g., a cannulated tapping instrument, cannulated screw, etc.) may be advanced along each K-wire (170) for insertion into pedicles (2). In some instances (e.g., after cannulated screws have been suitably positioned in pedicles (2), etc.), K-wires (170) may be removed from pedicles (2).

Figure 6C:
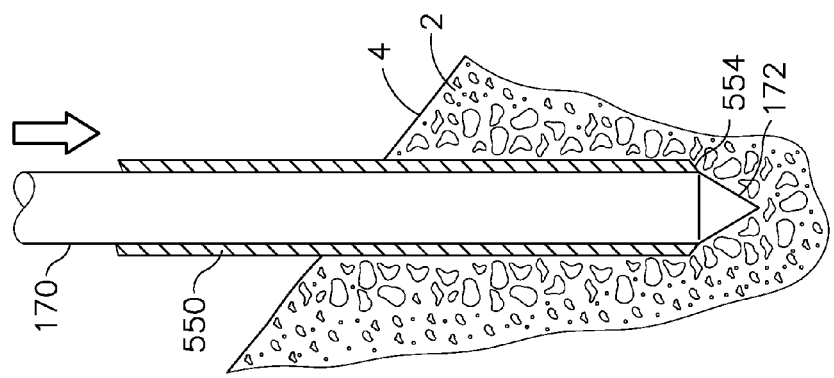
FIG. 6C depicts a side elevational view of the blade assembly of FIG. 6A, showing a K-wire inserted through the sheath and into the pedicle, with the pedicle shown in cross-section.
Figure 6B:
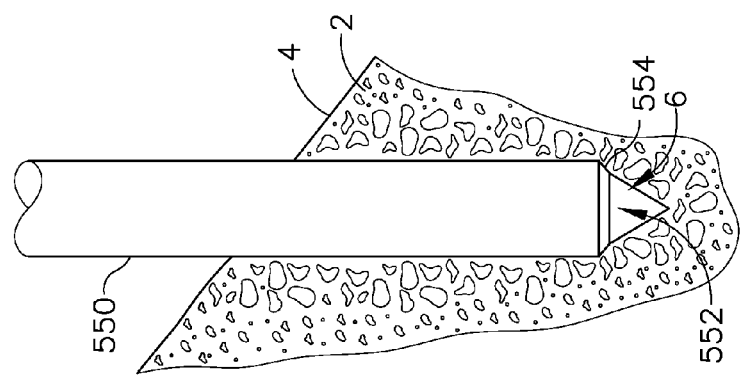
FIG. 6B depicts a side elevational view of the blade assembly of FIG. 6A, showing a blade removed from a sheath of the blade assembly, with the pedicle shown in cross-section.
Figure 6A:
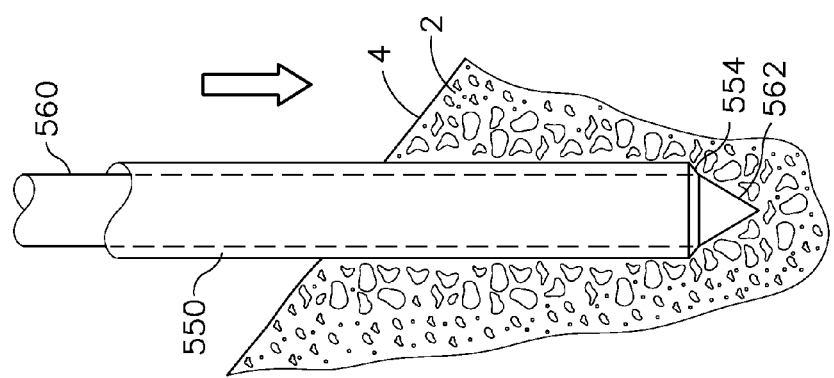
FIG. 6A depicts a side elevational view of another exemplary blade assembly suitable for use with the instrument of FIG. 2, being inserted within a pedicle of a vertebra, with the pedicle shown in cross-section.

FIGS. 6A-6C show an exemplary alternative blade (560) that may be incorporated into instrument (120) in place of blade (160). Blade (560) of this example is similar to blade (160), except that blade (560) is solid instead of being hollow, such that blade (560) has a closed, sharp distal end (562). Blade (560) of this example also has a sheath (550), which is slidably positioned coaxially about blade (560). Sheath (550) defines a lumen (552) and has an open distal end (554). In some instances, a plurality of nodal supports may be located within lumen (552), at locations corresponding to nodes of ultrasonic vibrations that are communicated through blade (560) when blade (560) is fully inserted in sheath (550). Such nodal supports may prevent blade (560) from transmitting ultrasonic vibrations to sheath (550). In some other versions, blade (560) and sheath (550) are in contact such that blade (560) transmits ultrasonic vibrations through sheath (550).

In an exemplary use, blade (560) is fully inserted in sheath (550) such that sharp distal end (562) of blade (560) protrudes distally from the open distal end (554) of sheath (550). With blade (560) and sheath (550) so arranged, the combination of blade (560) and sheath (550) are advanced distally into a pedicle (2) of a patient's vertebra, as shown in FIG. 6A. Of course, instrument (120) may instead be used to cut bone and/or other anatomical features elsewhere within a patient. Blade (560) is activated with ultrasonic vibrations during the insertion into pedicle (2). These ultrasonic vibrations promote penetration of the bone of pedicle (2) by blade (560). It should be understood that blade (560) may penetrate the bone of pedicle (2) even when sharp distal end (562) is oriented obliquely relative to the outer surface (4) of pedicle (2) as shown in FIG. 6A. The configuration of blade (560) and/or the ultrasonic vibration of blade (560) may prevent sharp distal end (562) from skiving or slipping along the outer surface (4) of pedicle (2).

Once blade (560) and sheath (550) reach a desired depth within pedicle (2), blade (560) is retracted proximally from sheath (550) while sheath (550) is left in pedicle (2), as shown in FIG. 6B. Once blade (560) has been completely retracted and removed from sheath (550), a K-wire (170) is inserted through lumen (552) of sheath (552) as shown in FIG. 6C. In particular, K-wire (170) is inserted such that sharp tip (172) of K-wire (170) protrudes distally from distal end (554) of sheath (550). Sheath (550) thus acts as a guide shaft for K-wire (170). Once K-wire (170) has been fully inserted through sheath (552), sheath (552) is withdrawn proximally, leaving K-wire (170) in pedicle (2).

Figure 7:
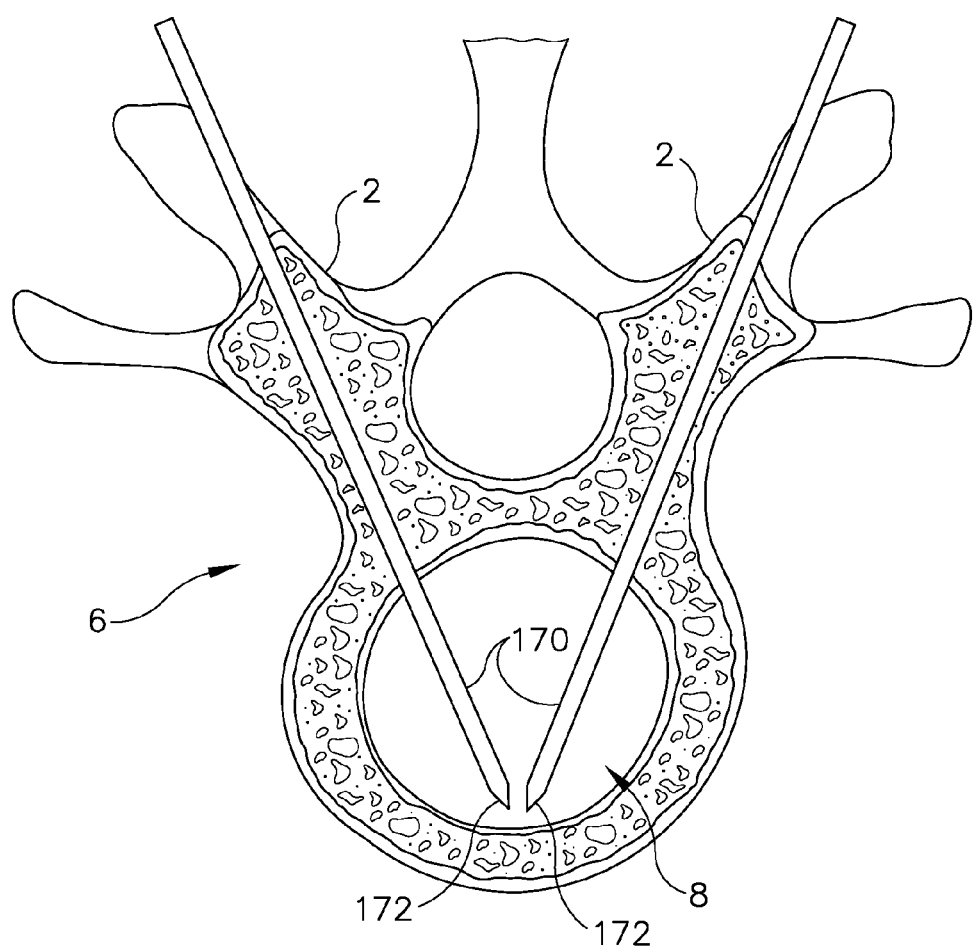
FIG. 7 depicts a cross sectional view of a vertebra, showing the K-wires of the blade assembly of FIG. 6A inserted within the pedicles of the vertebra.

FIG. 7 shows a vertebra (6) with a pair of K-wires (170) inserted therein. In particular, each K-wire (170) is inserted through a respective pedicle (2) of vertebra (6) such that the distal tip (172) of each pedicle (2) is located in the vertebral body (8). It should be understood that a version of instrument (120) using blade (160) or a version of instrument (120) using blade (560) may be used to position K-wires (170) as shown in FIG. 7. Of course, instrument (120) may also be used to perform a variety of other procedures in a variety of other locations.

Figure 8:
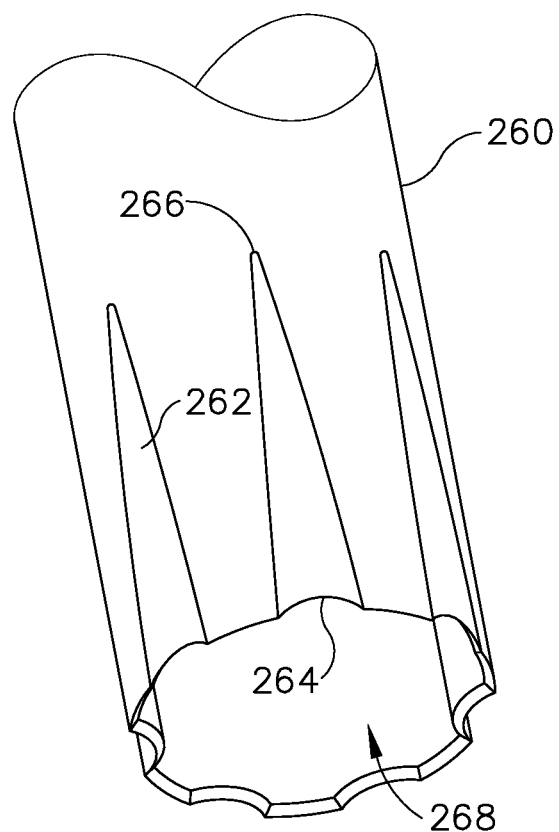
FIG. 8 depicts a partial perspective view of another exemplary blade suitable for use with the instrument of FIG. 2.
Figure 9:
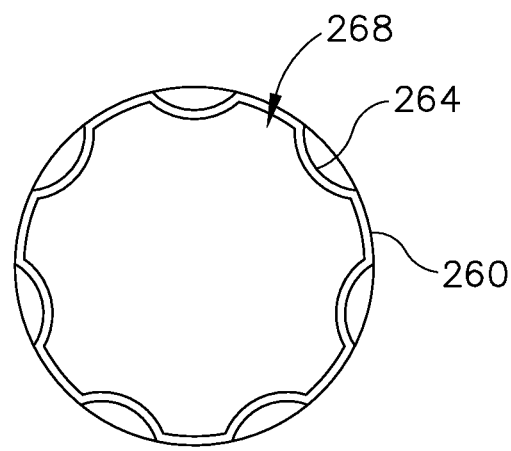
FIG. 9 depicts an end view of the blade of FIG. 8.

In some instances, it may be desirable to limit the depth of penetration of blade (160) in bone. Accordingly, FIGS. 8-9 show an exemplary alternative blade (260) that may be incorporated into instrument (120) in place of blade (160). Blade (260) of this example is similar to blade (160), such that blade (260) has a hollow tubular configuration defining a lumen (268). However, blade (260) of this example comprises a plurality of flutes (262) extending proximally from the distal end of blade (260). As best seen in FIG. 9, distal end (264) of flutes (262) have a semi-circular concave profile formed inwardly on blade (260). Although the present example shows distal end (264) of flutes (262) having a semi-circular profiles, other suitable concave profiles may be used (e.g., rectangular, square, triangular, etc.). Flutes (262) of the present example curve along a plane that is perpendicular to the longitudinal axis of blade (260). In some versions, flutes (260) also curve upwardly from the regions of distal end (264) that extend between flutes (260). Flutes (262) then taper proximally to respective tips (266), as shown in FIG. 8. Accordingly, flutes (262) may act to stop or significantly slow the penetration of blade (260) within a pedicle (2).

FIGS. 10A-10B show blade (260) entering pedicle (2). Ultrasonic energy is delivered to blade (260) to promote penetration of pedicle (2) by blade (260). As blade (260) penetrates pedicle (2), flutes (262) of blade (260) fill with material from pedicle (2) to thereby stall the ultrasonic energy at blade (260). Accordingly, once blade (262) has penetrated pedicle (2) to a sufficient depth to fill flutes (262), as shown in FIG. 10B, flutes (262) act to stop or slow blade (260). In other words, the distal advancement of blade (260) is halted or slowed once tips (266) reach the outer surface (4) of pedicle (2). Flutes (262) may have any length suitable to allow blade (260) to reach a desired depth within pedicle (2). A K-wire (170) may be inserted through lumen (268) into pedicle (2) once blade (260) has reached an appropriate depth within pedicle (2).

B. Exemplary Channeled Blade Assembly

Figure 11:
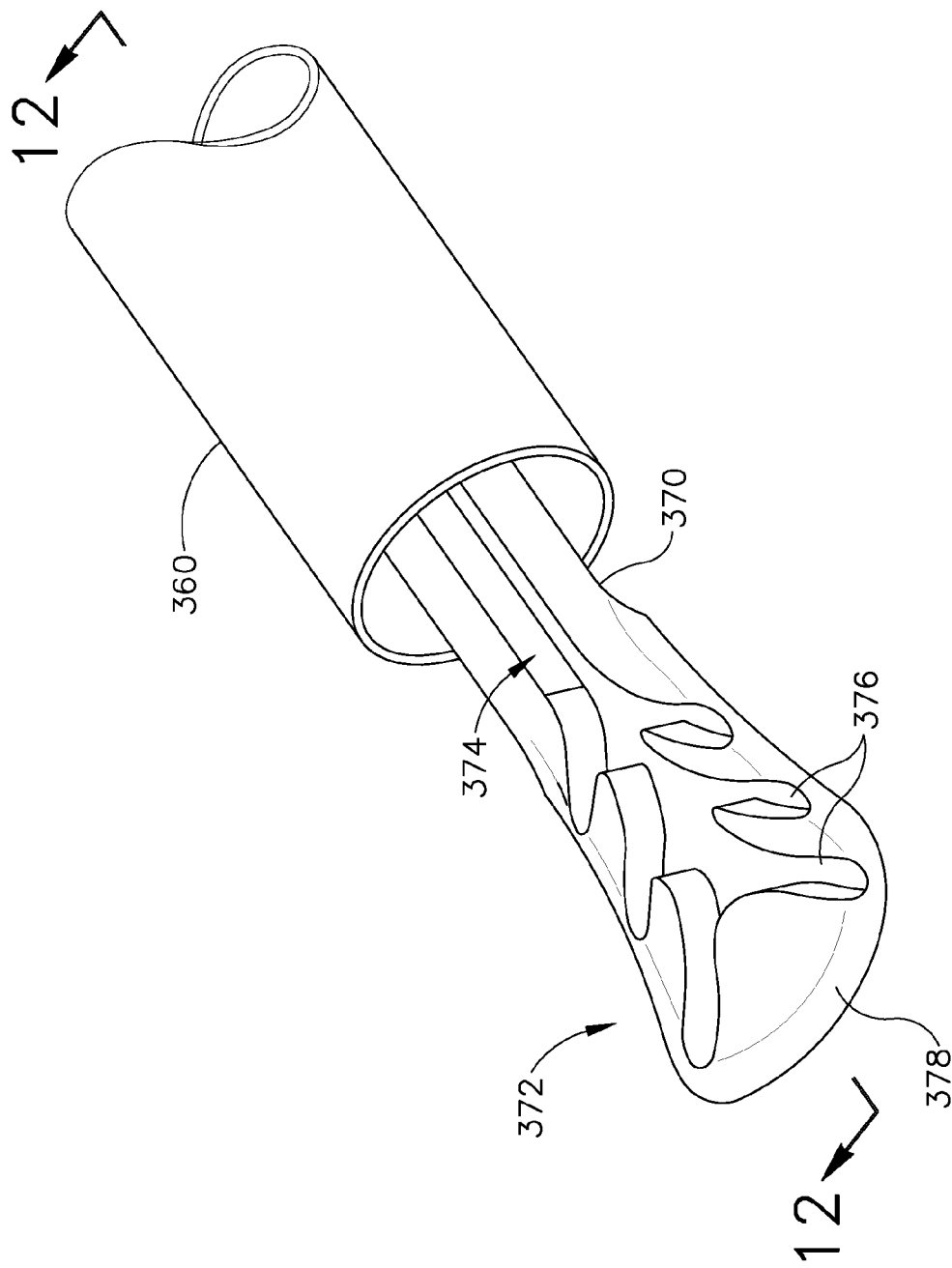
FIG. 11 depicts a partial perspective view of an exemplary blade assembly suitable for use with an ultrasonic surgical instrument of the system of FIG. 1.
Figure 12:
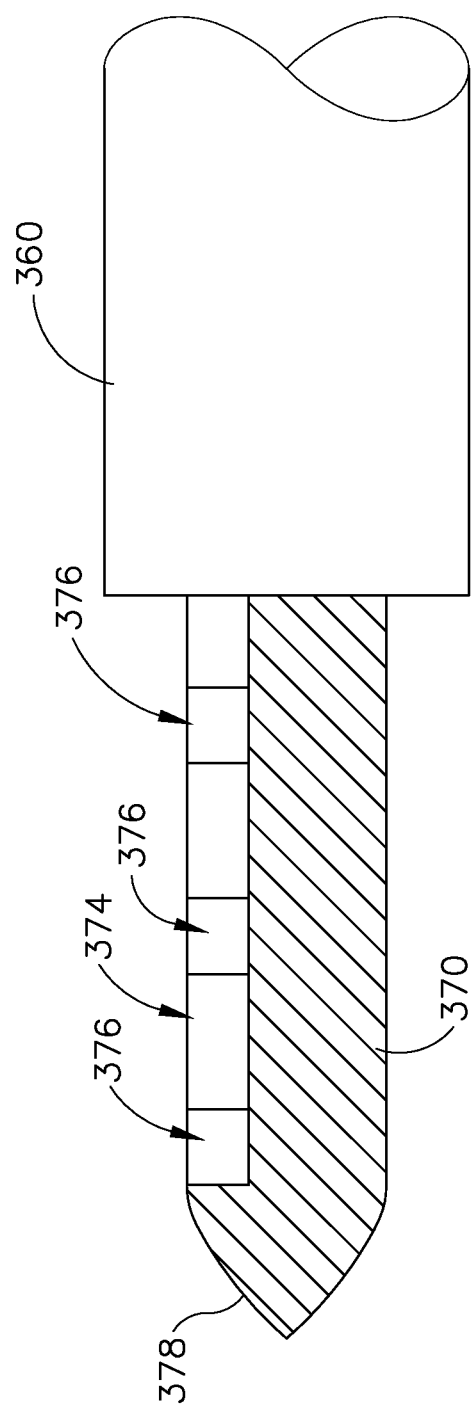
FIG. 12 depicts a cross sectional view of the blade assembly of FIG. 11, taken along line 12-12 of FIG. 11.

In some instances, it may be desirable to cut pedicle (2) without necessarily using the same instrument to cut pedicle (2) and introduce a K-wire (170) or other bone insertion element. For example, FIGS. 11-12 show an alternative exemplary blade assembly (372) for removing bone material. Blade assembly (372) comprises a blade (370) that extends distally from shaft (360), which may be incorporated into instrument (120) in lieu of blade (160). Blade (370) may be driven to vibrate ultrasonically like blade (160). Unlike blade (160), however, blade (370) of the present example comprises a paddle-shaped distal end (378) with a channel (374) extending laterally into blade (370) and proximally along an exterior surface of blade (370).

As best seen in FIG. 11, distal end (378) has a convex distal edge, flanked by concave side edges. It should be understood, however, that the distal edge may instead be concave; and/or that the side edges may be convex. As best seen in FIG. 12, the distal edge of distal end (378) is formed by the convergence of two surfaces that curve convexly along a vertical plane. In some other versions, the distal edge of distal end (378) is formed by the convergence of two surfaces that are flat yet angled toward each other along the vertical plane. In still other versions, the distal edge of distal end (378) is formed by the convergence of two surfaces that curve concavely along a vertical plane. Other suitable configurations will be apparent to those of ordinary skill in the art in view of the teachings herein.

The proximal end of channel (374) may be in fluid communication with a source of irrigation fluid (e.g., saline, etc.). In addition or in the alternative, the proximal end of channel (374) may be in fluid communication with a source of suction. In some versions, channel (374) is used to alternatingly communicate an irrigation fluid to the surgical site, then suction away fluid and debris. The distal end of channel (374) defines a plurality of recesses (376) extending outwardly from channel (374) on the exterior surface on the distal portion of blade (370). Recesses (376) are obliquely angled proximally relative to channel (374) and relative to the longitudinal axis of blade (370) such that recesses (376) provide a proximally oriented flow path to channel (374). This may assist in removal of bone material during use of blade (370) at the surgical site.

During an exemplary use of blade (370), ultrasonic energy is delivered to blade (370) to promote cutting of bone by blade (370). As blade (370) penetrates the bone, debris from the bone around or near the cutting area may be removed through recesses (376) and proximally through channel (374). Blade (370) may penetrate bone to remodel the bone, to provide an insertion site for an instrument guidance device, to provide an insertion site for an implant device, and/or for any other suitable purpose. Other suitable ways in which blade (370) may be used will be apparent to one with ordinary skill in view of the teachings herein.

Figure 13:
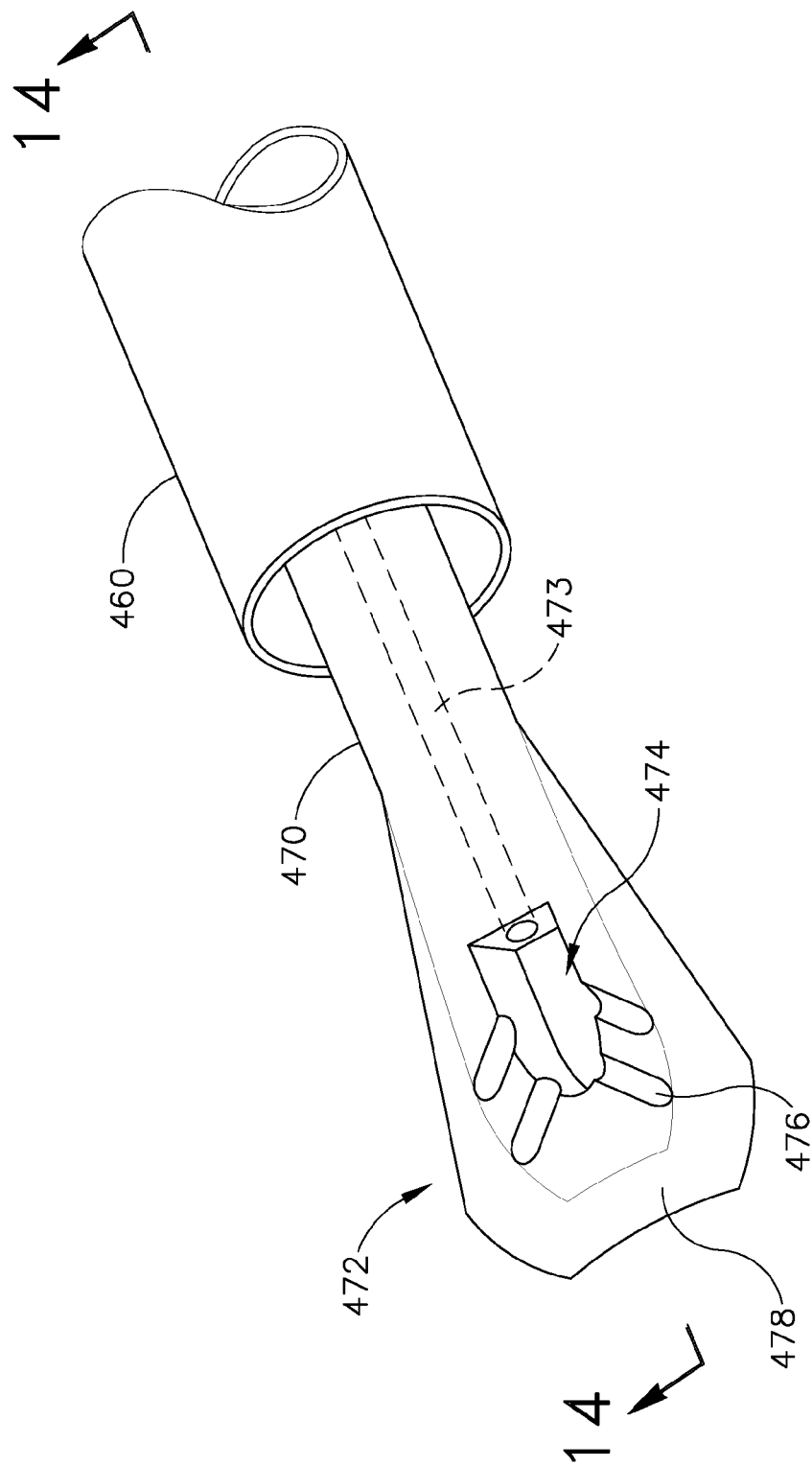
FIG. 13 depicts a partial perspective view of another exemplary blade assembly suitable for use with an ultrasonic surgical instrument of the system of FIG. 1.
Figure 14:
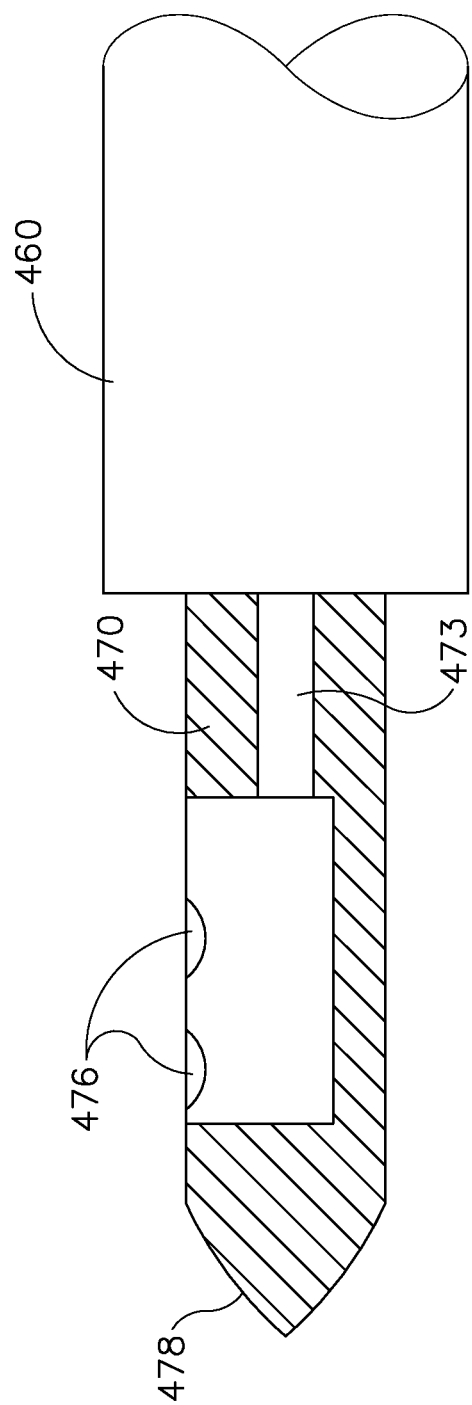
FIG. 14 depicts a cross sectional view of the blade assembly of FIG. 13, taken along line 14-14 of FIG. 13.

In some instances, it may be desirable to incorporate an irrigation fluid conduit in blade (370). For example, FIGS. 13-14 show blade assembly (472) that is similar to blade assembly (372), except that blade assembly (472) defines a lumen (473) extending through blade (470). Lumen (473) opens to a lateral recess (474) positioned within a distal portion of blade (470). A plurality of recesses (476) extends proximally and inwardly on the distal portion of blade (470) to recess (474). Recesses (476) are angled obliquely relative to recess (474) and relative to the longitudinal axis of blade (470). Lumen (473) may be in fluid communication with a source of irrigation fluid (e.g., saline, etc.). In addition or in the alternative, the proximal end of lumen (473) may be in fluid communication with a source of suction. In some versions, lumen (473) is used to alternatingly communicate an irrigation fluid to the surgical site, then suction away fluid and debris.

As best seen in FIG. 13, the distal end (478) of blade (470) is tapered and has a distal edge that is concave along a horizontal plane. In some other versions, the distal edge of distal end (478) is convex along a horizontal plane. As best seen in FIG. 14, the distal edge of distal end (478) is formed by the convergence of two surfaces that curve convexly along a vertical plane. In some other versions, the distal edge of distal end (478) is formed by the convergence of two surfaces that are flat yet angled toward each other along the vertical plane. In still other versions, the distal edge of distal end (478) is formed by the convergence of two surfaces that curve concavely along a vertical plane. Other suitable configurations will be apparent to those of ordinary skill in the art in view of the teachings herein.

Figure 15:
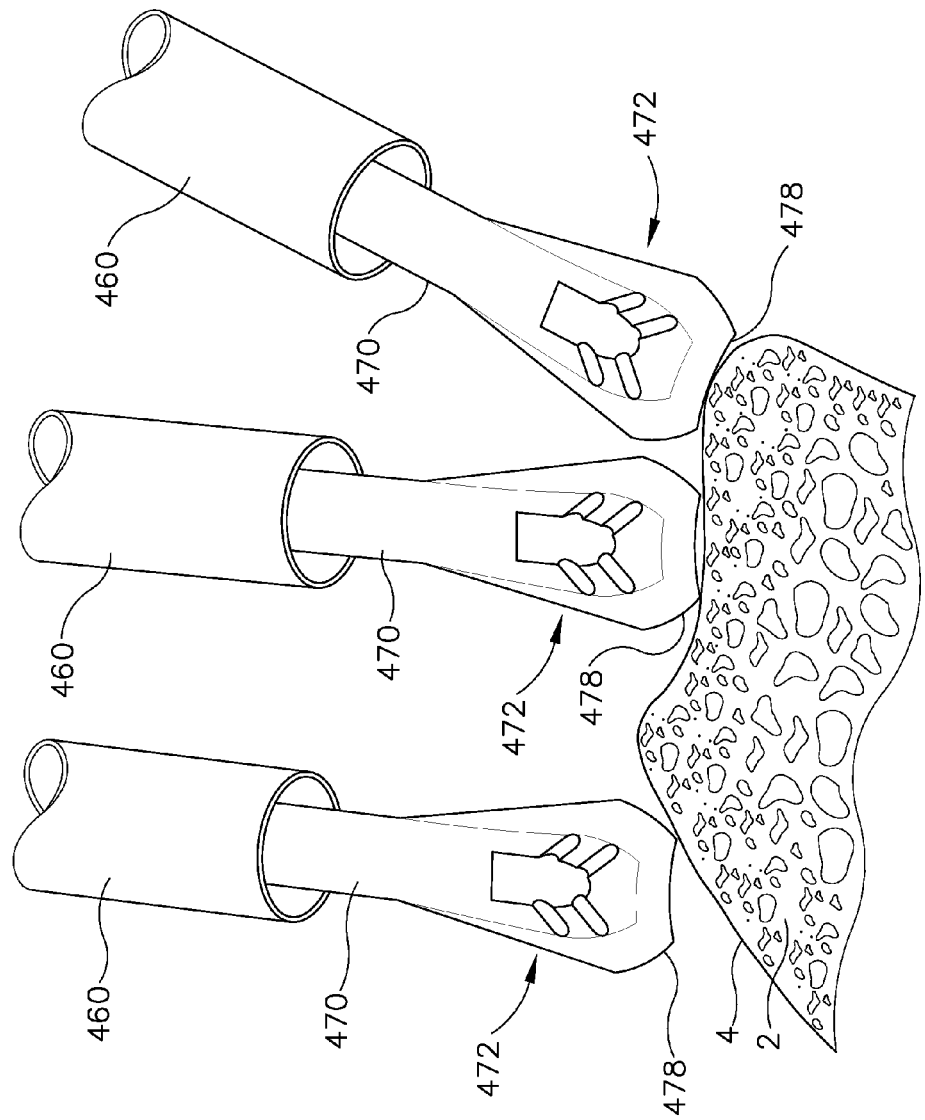
FIG. 15 depicts a top plan view of the blade assembly of FIG. 13 engaging a pedicle at various positions and orientations, with the pedicle shown in cross-section.

In the present example, the concave curvature of the distal edge of distal end (478) along a horizontal plane may reduce skiving or slipping of blade (470) against bone during operation. For instance, FIG. 15 shows several depictions of blade (470) engaged with various contours of the outer surface (4) of a pedicle (2). It should be understood that blade (470) may be driven distally against outer surface (4) of a pedicle (2) at any of these locations; and that the configuration of distal end (478) may substantially prevent blade (470) from slipping along outer surface (4).

Figure 16:
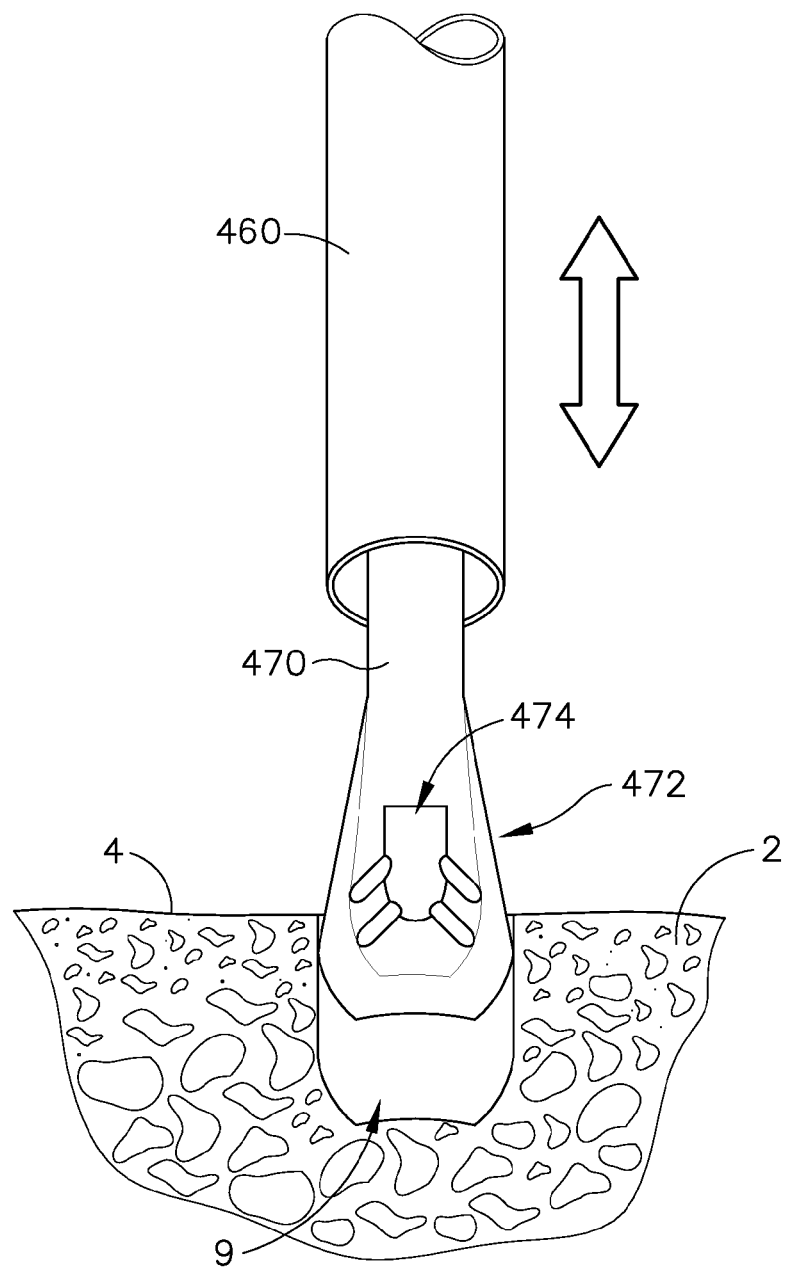
FIG. 16 depicts a top plan view of the blade assembly of FIG. 13 engaging in plunge cutting operation on a pedicle, with the pedicle shown in cross-section.

In an exemplary use of blade (470), ultrasonic energy is delivered to blade (470) to promote cutting of bone by blade (470). For instance, as shown in FIG. 16, blade (470) may be used to perform plunge cutting to form a recess (9) in pedicle (2) that is as wide as blade (470), to a depth associated with the proximal end of recess (474). As blade (470) penetrates the bone, debris from the bone around or near the cutting area may be removed through recesses (474, 476). Irrigation from irrigation source (118) may be supplied through lumen (473) of blade (470) to recess (474) to thereby flush debris from recesses (474, 476) and assist in removal of bone material. Blade (470) may penetrate bone to remodel the bone, to provide an insertion site for an instrument guidance device, to provide an insertion site for an implant device, and/or for any other suitable purpose. Other suitable ways in which blade (470) may be used will be apparent to one with ordinary skill in view of the teachings herein.

Figure 17:
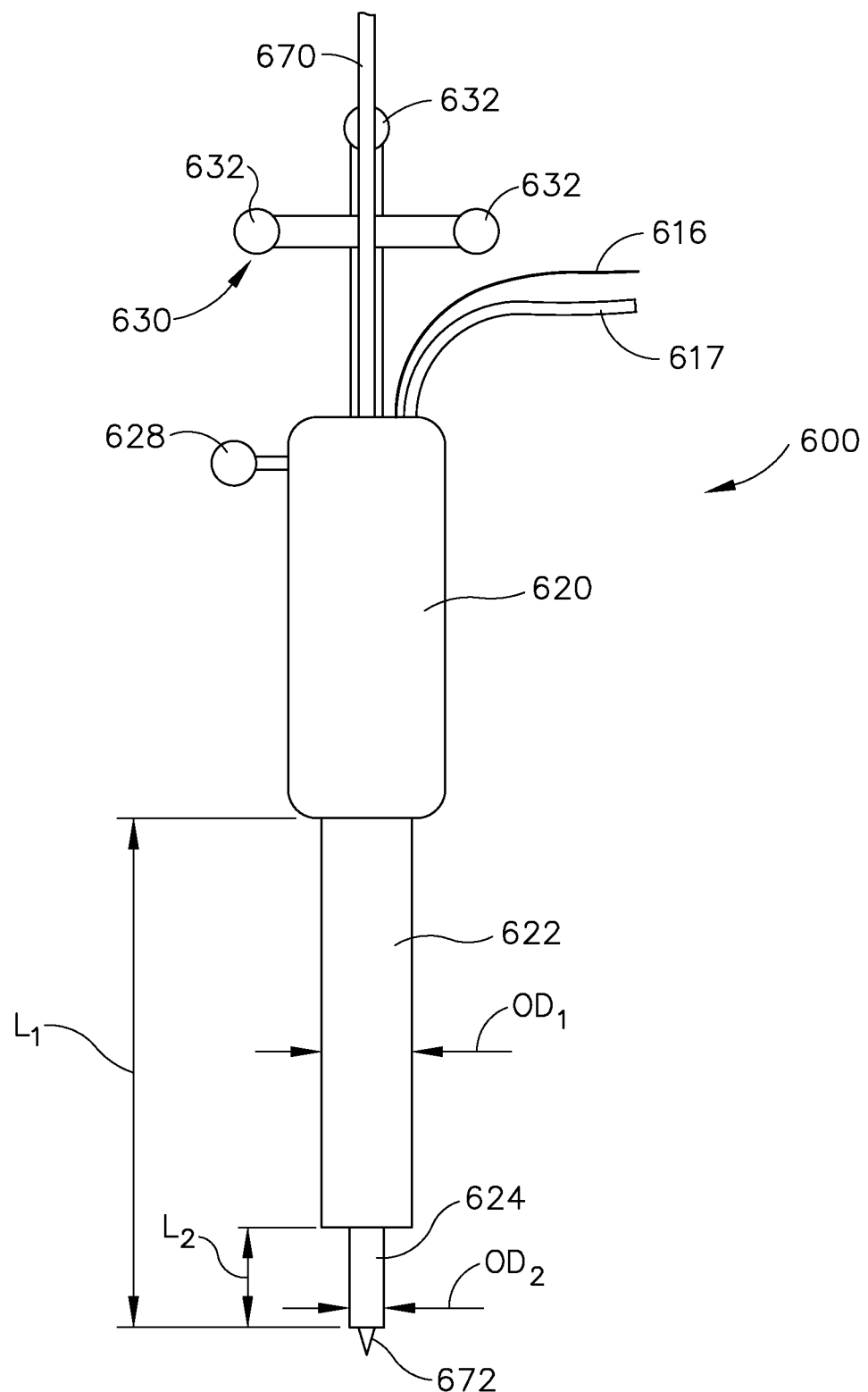
FIG. 17 depicts a front elevational view of another exemplary ultrasonic surgical instrument that may form part of the system of FIG. 1.

C. Exemplary Instrument with Integrated Imaging Features and Ultrasonically Activated K-Wire In some instances, it may be desirable to provide a version of instrument (20) that includes features allowing the operator to move and orient the instrument while keeping their hands out of the path of x-rays of an imaging system while using the imaging system to guide the instrument. In addition or in the alternative, it may be desirable to provide a version of instrument (20) that is operable to ultrasonically activate a k-wire (170), such that the distal tip (172) of k-wire (170) serves as an ultrasonic blade (24). FIG. 17 shows an example of an instrument (600) that provides such a capability. Instrument (600) of this example comprises a body (620), with a first shaft element (622) and a second shaft element (624) extending distally from body (620). Shaft elements (622, 624) are both hollow, are coaxially aligned with each other, and are longitudinally fixed in relation to each other and in relation to body (620). A K-wire (670) is slidably disposed within shaft elements (622, 624). The distal tip (672) of K-wire (670) is shown as protruding distally from the distal end of second shaft element (624).

An irrigation conduit (617) is coupled with body (620) and may be further coupled with a source of irrigation fluid (e.g., saline, etc.). In some versions, irrigation conduit (617) is configured to deliver irrigation fluid to one or more irrigation openings formed in second shaft element (624). In addition or in the alternative, irrigation conduit (617) may be configured to deliver irrigation fluid to a gap defined between the inner diameter of second shaft element (624) and the outer diameter of K-wire (670). Other suitable ways in which irrigation conduit (617) may deliver irrigation fluid to a surgical site will be apparent to those of ordinary skill in the art in view of the teachings herein. It should also be understood that irrigation conduit (617) and/or some other conduit may be used to provide suction to the surgical site. Irrigation fluid and/or suction may be used to clear debris (e.g., bone debris, etc.) from the surgical site.

Body (620) of the present example includes an ultrasonic transducer (not shown) that is coupled with a power source via a cable (616). The ultrasonic transducer is operable to convert electrical power into ultrasonic vibrations, like ultrasonic transducer (26) described above. In some versions, instrument (600) is further configured to enable the ultrasonic vibrations that are generated by the ultrasonic transducer to be communicated to K-wire (670), such that K-wire (670) vibrates ultrasonically when the ultrasonic transducer is activated. The distal end (672) of K-wire (670) may thus act as an ultrasonic blade (24). By way of example only, one or more features within body (620) may provide selective mechanical and acoustic engagement and disengagement between the ultrasonic transducer and K-wire (670). Such coupling features may provide mechanical and acoustic engagement between the ultrasonic transducer and K-wire (670) as K-wire (670) is driven into bone; then disengage K-wire (670) from the ultrasonic transducer to enable instrument (600) to be withdrawn from the patient along K-wire (670) while K-wire remains disposed in the bone. In addition to or as an alternative to K-wire (670) being ultrasonically activated by the ultrasonic transducer, second shaft element (624) may be mechanically and acoustically coupled with the ultrasonic transducer, such that second shaft element (624) may vibrate ultrasonically.

In the present example, first shaft element (22) has an outer diameter ($OD_1$) that is larger than the outer diameter ($OD_2$) of second shaft element (624). By way of example only, first shaft element (622) may have an outer diameter ($OD_1$) that is between approximately 10 mm and approximately 12 mm. Alternatively, any other suitable outer diameter may be used. Also by way of example only, second shaft element (624) may have an outer diameter ($OD_2$) that is less than approximately 3 mm. Alternatively, any other suitable outer diameter may be used. In the present example, the reduction in outer diameter ($OD_1$, $OD_2$) between first shaft element (622) and second shaft element (624) is stepped down suddenly, such that there is not a smooth transition from first shaft element (622) to second shaft element (624). This step-down configuration may enable the transition from first shaft element (622) to second shaft element (624) to act as a hard stop. For instance, if second shaft element (624) is inserted into bone, the sudden transition to the larger outer diameter ($OD_1$) at the distal end of first shaft element (622) may act as a hard stop to prevent further insertion into the bone. The inner diameter of second shaft element (624) may approximate the outer diameter of K-wire (670). By way of example only, the inner diameter of second shaft element (624) may be approximately 2 mm. Alternatively, any other suitable inner diameter may be used.

Shaft elements (622, 624) together define a length ($L_1$) that is sized to pass through an incision in the patient's skin, fascia, and muscle, thereby enabling the distal end of first shaft element (622) to reach bone and the distal end of second shaft element (624) to be inserted within the bone. By way of example only, this length ($L_1$) may be between approximately 100 mm and approximately 150 mm. Alternatively, any other suitable length may be used. Also in the present example, second shaft element (624) has a length ($L_2$) that is selected to approximate the average depth of a pedicle (2). By way of example only, this length ($L_1$) may be between approximately 20 mm and approximately 25 mm. Alternatively, any other suitable length may be used.

Body (620) of the present example further comprises a coupling feature (628) that enables body (620) to be detachably coupled with an operator manipulation feature. By way of example only, a radiolucent handle or handle assembly may be coupled with coupling feature (628). This may allow the operator to maneuver and orient instrument (600) by grasping the radiolucent handle or handle assembly. The radiolucent handle or handle assembly may be configured to enable the operator's grasping hand to be positioned out of the path of x-rays that are used to provide visualization of instrument (600) and the target vertebra through a fluoroscopic imaging system. Various suitable configurations for handles or handle assemblies that may be secured to coupling feature (628) will be apparent to those of ordinary skill in the art in view of the teachings herein. It should also be understood that coupling feature (628) is merely optional and need not necessarily be included.

Body (620) of the present example further comprises a navigation assembly (630), which is removably secured to a proximal end of body (620). Navigation assembly (630) includes an array of radiopaque elements (632). The radiopaque nature of radiopaque elements (632) and the positioning of radiopaque elements (632) may facilitate positioning of instrument (600) under fluoroscopic guidance. It should also be understood that navigation assembly (630) may be configured for use with other kinds of imaging modalities. Various suitable forms that navigation assembly (630) may take will be apparent to those of ordinary skill in the art in view of the teachings herein. In some versions, navigation assembly (630) is simply omitted.

In an exemplary use of instrument (600), shaft elements (622, 624) are inserted through a patient's skin, fascia, and muscle until distal tip (672) of K-wire (670) and/or the distal end of second shaft element (624) engages the outer surface (4) of a pedicle (2). Distal tip (672) of K-wire (670) may protrude distally from the distal end of second shaft element (624) during such insertion. In some instances, distal tip (672) and/or second shaft element (624) is vibrating ultrasonically during such insertion through the patient's skin, fascia, and muscle. In some other versions, conventional instruments and techniques are used to clear a path through the patient's skin, fascia, and muscle to enable distal tip (672) of K-wire (670) and/or the distal end of second shaft element (624) to engage the outer surface (4) of pedicle (2). In either case, with distal tip (672) of K-wire (670) and/or the distal end of second shaft element (624) engaging the outer surface (4) of a pedicle (2), the ultrasonic transducer is activated to vibrate distal tip (672) of K-wire (670) and/or the distal end of second shaft element (624) ultrasonically, enabling distal tip (672) of K-wire (670) and the distal end of second shaft element (624) to be driven distally into pedicle (2).

Distal tip (672) of K-wire (670) and the distal end of second shaft element (624) are driven distally into pedicle (2) until substantially the full length ($L_2$) of second shaft element (624) is disposed in pedicle (2). At this point, the stepped transition from the smaller outer diameter ($OD_1$) of second shaft element (624) to the larger outer diameter ($OD_2$) of first shaft element (622) engages the outer surface (4) of pedicle (2), providing a hard stop. This hard stop may provide the operator with tactile feedback indicating that instrument (600) has achieved a suitable insertion depth. At this stage, the operator may further drive K-wire (670) into pedicle (2), leaving shaft elements (622, 624) stationary, if desired. The operator may then withdraw instrument (600) from the patient, leaving K-wire (670) disposed in pedicle (2). In versions where K-wire (670) is mechanically and acoustically coupled with the ultrasonic transducer in body (620), K-wire (670) may be mechanically and acoustically de-coupled from the ultrasonic transducer in body (620) before instrument (600) is withdrawn from the patient. It should also be understood that irrigation fluid and/or suction may be provided through conduit (617) at one or more stages before instrument (600) is withdrawn from the patient, to clear debris from the insertion site.

After instrument (600) is withdrawn from the patient, one or more devices may be advanced along K-wire (670). By way of example only, a cannulated tapping instrument may be passed along K-wire (670) to tap an opening in pedicle (2). The cannulated tapping instrument may then be withdrawn along K-wire (670); and then a cannulated screw may be passed along K-wire (670) to thread into a threaded bore formed by the cannulated tapping instrument. Once the cannulated screw is suitably positioned in pedicle (2), K-wire (670) may be removed from pedicle (2). Other suitable ways in which instrument (600) may be used will be apparent to those of ordinary skill in the art in view of the teachings herein.

III. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system, comprising:
   (a) an ultrasonic instrument comprising:
      (i) an ultrasonic transducer, wherein the ultrasonic transducer is operable to convert electrical power into ultrasonic vibrations,
      (ii) an ultrasonic blade extending longitudinally and having a radially cylindrical outer surface in acoustic communication with the ultrasonic transducer such that the ultrasonic transducer is operable to drive the ultrasonic blade to vibrate ultrasonically, wherein the ultrasonic blade is operable to form an opening within bone, and
      (iii) a fluid conduit configured to fluidly connect to an irrigation fluid source for receiving a fluid therefrom, wherein the fluid conduit is configured to communicate the fluid therethrough from the irrigation fluid source and provide the fluid from the ultrasonic instrument to a surgical site; and
   (b) a bone insertion element, wherein the bone insertion element is configured to be inserted within the opening formed by the ultrasonic blade.

2. The system of claim 1, wherein the bone insertion element comprises a K-wire.

3. The system of claim 1, wherein the ultrasonic blade defines a lumen.

4. The system of claim 1, wherein the lumen is configured to receive the bone insertion element.

5. The system of claim 1, further comprising an irrigation fluid source associated with the ultrasonic blade.

6. The system of claim 5, wherein the irrigation fluid source is operable to deliver fluid within an interior region of the blade.

7. The system if claim 6, wherein the irrigation fluid source is operable to deliver fluid within a gap defined between the blade and the bone insertion element.

8. The system of claim 1, wherein the bone insertion element is coaxially disposed within the ultrasonic blade.

9. The system of claim 1, further comprising a sheath, wherein the sheath is configured to slidably receive the ultrasonic blade, wherein the sheath is further configured to slidably receive the bone insertion element.

10. The system of claim 1, wherein the ultrasonic blade has a distal end with a plurality of flutes.

11. The system of claim 1, wherein the instrument includes a proximal port configured to receive the bone insertion element.

12. The system of claim 11, wherein the proximal port is coaxially aligned with the blade.

13. The system of claim 1, wherein the ultrasonic instrument has a distal opening in fluid communication with the fluid conduit, wherein the fluid conduit is configured to provide the fluid through the distal opening to the surgical site.

14. The system of claim 13, wherein the ultrasonic blade includes a lumen, wherein the lumen extends to the distal opening and is fluidly connected to the fluid conduit.

15. The system of claim 1, wherein the ultrasonic blade has a distal tubular end portion, wherein the distal tubular end portion has at least a portion of a lumen extending therethrough and is configured to receive the bone insertion element.

16. The system of claim 1, wherein the ultrasonic blade has a distal blade portion configured to be received within the bone, wherein the distal blade portion has a distal end defining an outer radial profile, and wherein the distal blade portion that projects proximally from the distal end is positioned radially within the outer radial profile of the distal end.

17. The system of claim 1, wherein the ultrasonic blade has a distal edge positioned at an anti-node such that the distal edge is configured to be ultrasonically vibrated.

18. A system, comprising:
   (a) an ultrasonic instrument comprising:
      (i) an ultrasonic transducer, wherein the ultrasonic transducer is operable to convert electrical power into ultrasonic vibrations, and
      (ii) an ultrasonic blade in acoustic communication with the ultrasonic transducer such that the ultrasonic transducer is operable to drive the ultrasonic blade to vibrate ultrasonically, wherein the ultrasonic blade includes a lumen extending therethrough and is operable to form an opening within bone, wherein the ultrasonic blade has a distal tubular end portion with a distal edge, wherein the distal tubular end portion has at least a portion of the lumen extending therethrough to the distal edge and the distal edge is positioned at an anti-node such that the distal edge is configured to be ultrasonically vibrated; and
   (b) a bone insertion element, wherein the bone insertion element is configured to be inserted within the opening formed by the ultrasonic blade.

19. A system, comprising:
   (a) an ultrasonic instrument comprising:
      (i) an ultrasonic transducer, wherein the ultrasonic transducer is operable to convert electrical power into ultrasonic vibrations, and
      (ii) an ultrasonic blade in acoustic communication with the ultrasonic transducer such that the ultrasonic transducer is operable to drive the ultrasonic blade to vibrate ultrasonically, wherein the ultrasonic blade includes a lumen extending therethrough and is operable to form an opening within bone, and wherein the ultrasonic blade has a distal blade portion configured to be received within the bone, wherein the distal blade portion has a distal end defining an outer radial profile, and wherein the distal blade portion that projects proximally from the distal end is positioned radially within the outer radial profile of the distal end; and
   (b) a bone insertion element configured to be received within the lumen, wherein the bone insertion element is configured to be inserted within the opening formed by the ultrasonic blade.

* * * * *